United States Patent

Bank

[11] Patent Number: 5,326,894
[45] Date of Patent: Jul. 5, 1994

[54] β-CYANOALKYLSILANE PREPARATION USING DIVINYLBENZENE/4-VINYLPYRIDINE COPOLYMER RESIN AS CATALYST

[75] Inventor: Howard M. Bank, Freeland, Mich.

[73] Assignee: Dow Corning Corporation, Midland, Mich.

[21] Appl. No.: 155,899

[22] Filed: Nov. 23, 1993

[51] Int. Cl.$^5$ ................................ C07F 7/10
[52] U.S. Cl. .................................... 556/415
[58] Field of Search ......................... 556/415

[56] References Cited

U.S. PATENT DOCUMENTS

| | | | |
|---|---|---|---|
| 2,906,764 | 9/1959 | Jex et al. | 556/415 |
| 2,971,970 | 2/1961 | Bluestein | 556/415 |
| 2,971,972 | 2/1961 | Bluestein | 556/415 |
| 3,180,882 | 4/1965 | Jex et al. | 556/415 |
| 3,257,440 | 6/1966 | Jex | 556/415 |
| 4,113,845 | 9/1978 | Litteral | 556/415 |
| 5,103,033 | 4/1992 | Bank | 556/415 |
| 5,126,468 | 6/1992 | Bank | 556/415 |
| 5,126,469 | 6/1992 | Bank | 556/415 |
| 5,247,109 | 9/1993 | Bank | 556/415 |
| 5,247,110 | 9/1993 | Bank | 556/415 |
| 5,262,554 | 11/1993 | Bank | 556/415 |

OTHER PUBLICATIONS

Pike et al., J. Org. Chem. 24, 1939–42, 1959.
Pike et al., J. Org. Chem. 27, 2190–92, 1962.
Rajkamur et al., Organometallics 8, 549–550, 1989.

Primary Examiner—Paul F. Shaver
Attorney, Agent, or Firm—William F. Boley

[57] ABSTRACT

A process for the preparation of hydrolyzable β-cyanoalkylsilanes. More particularly, this invention relates to the catalytic addition of silicon hydrides to α,β-unsaturated olefinic nitriles to form β-cyanoalkylsilanes. The present invention employs a divinylbenzene/4-vinylpyridine copolymer based resin as catalyst.

13 Claims, No Drawings

β-CYANOALKYLSILANE PREPARATION USING DIVINYLBENZENE/4-VINYLPYRIDINE COPOLYMER RESIN AS CATALYST

BACKGROUND OF THE INVENTION

The present invention is a process for the preparation of hydrolyzable beta-cyanoalkylsilanes. More particularly, this invention relates to the catalytic addition of silicon hydrides to α,β-unsaturated olefinic nitriles to form β-cyanoalkylsilanes. The present invention employs a divinylbenzene/4-vinylpyridine copolymer based resin as catalyst.

Hydrolyzable beta-cyanoalkylsilanes are useful for the production of polyorganosiloxanes containing the beta-cyanoalkyl substituent. The silicon-bonded beta-cyanoalkyl radical is extremely resistant to hydrolysis and cleavage under hot, humid conditions. Therefore, beta-cyanoalkylsilanes find particular use in the preparation of polyorganosiloxanes which must be subjected to hot, humid conditions. The presence of the silicon-bonded beta-cyanoalkyl radical substituted on polyorganosiloxanes also tends to stabilize the polyorganosiloxanes against swelling induced by liquid hydrocarbons.

Jex et al., U.S. Pat. No. 2,906,764, issued Sep. 29, 1959, describe a process for producing cyanoalkylsilanes by reacting an olefinic nitrile with a silane, the silane having at least one hydrogen and one hydrolyzable group bonded to the silicon atom, in the presence of a diarylamine catalyst.

Pike et al., J. Org. Chem. 24, 1939–42, 1959, describe tertiary amines as effective directive catalysts for the reaction of trichlorosilane with acrylonitrile to form beta-cyanoethyltrichlorosilane.

Pike et al., J. Org. Chem. 27, 2190–92, 1962, describe preparation of beta-cyanoethyltrichlorosilane by reacting trichlorosilane with acrylonitrile in the presence of silylamine catalysts of the general formula $(CH_3)_3SiNR_2$, where the nitrogen atom of the silylamine is attached to the silicon atom.

Bluestein, U.S. Pat. No. 2,971,970, issued Feb. 14, 1961, describes a process for reacting hydrolyzable silicon hydride with an α,β-unsaturated olefinic nitrile to form a cyanoalkylsilane where the catalyst comprises (A) a cuprous compound, (B) a diamine, and (C) a trialkylamine.

Bluestein, U.S. Pat. No. 2,971,972, issued Feb. 14, 1961, describes a process for reacting phenyldichlorosilane and acrylonitrile to form β-cyanoethylphenyldichlorosilane without the necessity for employing a diamine. The process is conducted in the presence of a cuprous compound selected from a group consisting of cuprous oxide and cuprous halides, and in the presence of a trialkylamine.

Rajkumar et al., Organometallics 8, 549–550, 1989, describe a catalyst system consisting of tetramethylethylenediamine and cuprous oxide for the hydrosilylation of acrylonitrile to give the β-adduct.

Bank, U.S. Pat. No. 5,126,468, issued Jun. 30, 1992, describes a process for the preparation of hydrolyzable β-cyanoalkylsilanes by the catalytic addition of hydrolyzable silicon hydrides to α,β-unsaturated olefinic nitriles. The process employs a catalyst comprising a diamine and nonactivated copper or a compound of copper selected from a group consisting of copper metal, Cu(II) halide, Cu(II) oxide, copper sulfate, copper sulfide, and copper cyanide compounds, Cu(I) thiocyanide, and copper chromium compounds.

Bank, U.S. Pat. No. 5,126,469, issued Jun. 30, 1992, describes a process for the preparation of hydrolyzable β-cyanoalkylsilanes by the catalytic addition of hydrolyzable silicon hydrides to α,β-unsaturated olefinic nitriles using a supported catalyst. The supported catalyst comprises a diamine and supported copper or a supported copper compound.

SUMMARY OF INVENTION

A process for the preparation of hydrolyzable betacyanoalkylsilanes. More particularly, this invention relates to the catalytic addition of silicon hydrides to α,β-unsaturated olefinic nitriles to form β-cyanoalkylsilanes. The present invention employs a divinylbenzene/4-vinylpyridine copolymer based resin as catalyst.

DESCRIPTION OF INVENTION

The present invention is a process for preparation of betacyanoalkylsilanes described by formula:

(1)

The process comprises contacting a silicon hydride described by formula $$HSiX_3 \qquad (2)$$

with an unsaturated olefinic nitrile described by formula $$YCH{=}CCN, \qquad (3)$$

in the presence of a divinylbenzene/4-vinylpyridine copolymer based resin catalyst at a temperature within a range of about 50° C. to 250° C.; where X is a halogen and each Y is independently selected from a group consisting of hydrogen and lower alkyl radicals comprising one to eight carbon atoms.

The described process is applicable to the production of beta-cyanoalkylsilanes containing one silicon-bonded beta-cyanoalkyl radical, as described by Formula 1. Beta-cyanoalkylsilanes that can be made by the present process are, for example, beta-cyanoethyltrichlorosilane, beta-cyanopropyltrichlorosilane, beta-cyanobutyltrichlorosilane, beta-cyano-tert-butyltrichlorosilane, beta-cyanopentyltrichlorosilane, beta-cyanopropyltrichlorosilane, beta-cyanohexyltrichlorosilane, beta-cyanoheptyltrichlorosilane, beta-cyanooctyltrichlorosilane, alpha-methyl-beta-cyanoethyltrichlorosilane, alpha-ethyl-beta-cyanoethyltrichlorosilane, alpha-octyl-beta-cyanopropyltrichlorosilane, beta-cyanoethyltribromosilane, and beta-cyanopropyltrifluorosilane. The preferred beta-cyanoalkylsilane made by the present process is beta-cyanoethyltrichlorosilane.

The silicon hydride, described by Formula 2, contains one silicon-bonded hydrogen atom and three silicon-bonded halogen atoms. The halogen atom, X, can be selected from a group consisting of bromine, chlorine, fluorine, and iodine. The preferred halogen is chlorine.

The silicon hydride is contacted with an α,β-unsaturated olefinic nitrile described by Formula 3. The α,β-unsaturated olefinic nitrile contains substituents Y which are independently selected from a group consisting of hydrogen and lower alkyl radicals comprising from one to eight carbon atoms. For example, Y can be methyl, ethyl, propyl, butyl, tert-butyl, pentyl, hexyl, heptyl, and octyl. Examples of the α,β-unsaturated olefinic nitrile include acrylonitrile, methacrylonitrile, crotononitrile, ethylacrylonitrile, 1- cyanobutene-1, and 2-cyanooctene-1. The preferred α,β-unsaturated olefinic nitrile is acrylonitrile.

The molar ratio of the silicon hydride to the α,β-unsaturated olefinic nitrile may be varied within wide limits, however no particular advantage is derived from employing a molar excess of either reactant. The use of molar excesses of either of the two reactants is not precluded. It is preferred that the molar ratio of silicon hydride to α,β-unsaturated olefinic nitrile be within a range of about 0.5 to 1.5. In the most preferred embodiment of the invention, the molar ratio of silicon hydride to α,β-unsaturated olefinic nitrile is about 1.0.

The silicon hydride and α,β-unsaturated olefinic nitrile are contacted in the presence of a divinylbenzene/4-vinylpyridine copolymer based resin catalyst. General methods for making such catalyst are discussed in, for example, Litteral, U.S. Pat. No. 4,113,845, issued Sep. 12, 1978, which is incorporated herein by reference. Such catalyst are also available commercially as, for example, Reillex TM 402 and Reillex TM 425, Reilly Industries Inc., Indianapolis, Ind. The catalyst may be employed in the process, for example, as beads or as a powder. Generally, the smaller the size of the catalyst the greater the surface area and consequently the greater the activity of the catalyst. Examples of catalyst particle sizes useful in the present invention are provided in the examples herein. The catalyst can be a macroreticulated resin formed from a divinylbenzene/4-vinylpyridine copolymer.

The amount of catalyst employed in the present process in relation to the amount of α,β-unsaturated olefinic nitrile may be varied within wide limits and is dependent upon such conditions as the temperature at which the process is run, the surface area of the catalyst, and whether the process is run as a batch or continuous process. In general, the process can be run under conditions where the catalyst is present at about 0.1 to 50 weight percent of a mixture comprising the catalyst, the α,β-unsaturated olefinic nitrile, and the silicon hydride. Preferred is when the catalyst comprises about 0.5 to 30 weight percent of the mixture.

The silicon hydride, the α,β-unsaturated olefinic nitrile and the catalyst are contacted in a suitable reactor of standard design. The process can be run as a batch process, a semi-batch process, or a continuous process. A preferred process is where the reaction is conducted as a continuous process in a packed-bed reactor.

The temperature for conducting the process can be within a range of about 50° C. to 250° C. It is preferred that the temperature be within a range of about 80° C. to 200° C. Generally, higher temperatures allow the use of a lower catalyst concentration.

The pressure under which the process is conducted is not critical. Generally, the process can be run at a pressure within a range of about 0 psig to 1000 psig. Preferred is a pressure within a range of about 0 psig to 100 psig.

The time required for conducting the process may vary depending on the particular silicon hydride, α,β-unsaturated olefinic nitrile, temperature, and catalyst concentration employed. In general, reaction times of 0.1 to 30.0 hours are useful. A preferred reaction time is about 0.5 to 20.0 hours.

The following example is given to illustrate the present invention. This example is not intended to limit the present claims.

EXAMPLE 1

The ability of a divinylbenzene/4-vinylpyridine copolymer based resin to catalyze the addition of trichlorosilane to acrylonitrile to form cyanoethyltrichlorosilane was evaluated in a series of runs.

The runs were conducted in sealed glass tubes purged with argon. The runs were conducted by placing the weight and type of catalyst given in Table 1 into a tube, then adding to each tube 2 mL of a mixture of 0.0122 mole of trichlorosilane and 0.0116 mole of acrylonitrile. The tubes were sealed then heated for two hours at 150° C. The catalyst tested consisted of Reillex TM 425 (Reilly Industries Inc., Indianapolis, Ind.) and Reillex TM 402. Reillex 425 is divinylbenzene/4-vinylpyridine copolymer resin beads of size 18–50 mesh. Reillex 402 is divinylbenzene/4-vinylpyridine copolymer resin powder of about 60 mesh. The catalyst used in run number 4 was reused for run number 5.

The results of these runs are presented in Table 1. The contents of individual tubes were analyzed by gas liquid chromatography(GLC) using a thermal conductivity detector(TCD). The results are expressed as the area percent(Area %) under the GLC-TCD trace for β-cyanoethyltrichlorosilane, as a percentage of the total area under the GLC-TCD trace.

TABLE 1

Divinylbenzene/4-Vinylpyridine Copolymer Based Resin
Catalyzed Reaction of Trichlorosilane With Acrylonitrile

| Run No. | Catalyst Type | Catalyst Wt. | Area % β-Cyanoethyltrichlorosilane |
|---|---|---|---|
| 1 | Reillex 425 | 0.326 | 67.0 |
| 2 | Reillex 425 | 0.034 | 21.3 |
| 3 | Reillex 425 | 0.011 | 5.5 |
| 4 | Reillex 425 | 0.304 | 66.2 |
| 5 | *Reillex 425 | *.* | 63.9 |
| 6 | Reillex 402 | 0.011 | 28.5 |

(*The catalyst from run number 4 was reused in this run.)

I claim:

1. A process for preparation of beta-cyanoalkylsilanes described by formula

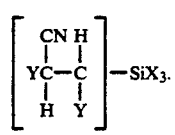

(1)

the process comprising: contacting a silicon hydride described by formula

with an unsaturated olefinic nitrile described by formula $$\text{YCH}=\text{CCN},\quad\begin{matrix}\text{Y}\\ \end{matrix} \qquad (3)$$

in the presence of a divinylbenzene/4-vinylpyridine copolymer based resin catalyst at a temperature within a range of about 50° C. to 250° C.; where X is a halogen and each Y is independently selected from a group consisting of hydrogen and lower alkyl radicals comprising one to eight carbon atoms.

2. A process according to claim 1, where the temperature is within a range of 80° C. to 200° C.

3. A process according to claim, 1, where the halogen is chlorine.

4. A process according to claim 1, where the silicon hydride is trichlorosilane.

5. A process according to claim 1, where the unsaturated olefinic nitrile is selected from a group consisting of acrylonitrile, methacrylonitrile, crotononitrile, ethylacrylonitrile, 1-cyanobutene-1, and 2-cyanooctene-1.

6. A process according to claim 1, where the unsaturated olefinic nitrile is acrylonitrile.

7. A process according to claim 1, where the beta-cyanoalkylsilane is beta-cyanoethyltrichlorosilane.

8. A process according to claim 1, where the silicon hydride is trichlorosilane, the unsaturated olefinic nitrile is acrylonitrile and the temperature is within a range of about 80° C. to 200° C.

9. A process according to claim 1, where the mole ratio of silicon hydride to unsaturated olefinic nitrile is about 1.0.

10. A process according to claim, 1, where the process is conducted for a time period in a range of about 0.1 to 30 hours.

11. A process according to claim 1, where the process is conducted as a continuous process in a packed-bed reactor.

12. A process according to claim 1, where the catalyst is present at about 0.1 to 50 weight percent of a mixture comprising the catalyst, the unsaturated olefinic nitrile, and the silicon hydride.

13. A process according to claim 1, where the catalyst is present at about 0.5 to 30 weight percent of a mixture comprising the catalyst, the unsaturated olefinic nitrile, and the silicon hydride.

* * * * *